(12) United States Patent
Perthu

(10) Patent No.: US 11,679,207 B2
(45) Date of Patent: Jun. 20, 2023

(54) INJECTION DEVICE AND ADAPTOR

(71) Applicant: UNION MEDICO APS, Copenhagen (DK)

(72) Inventor: Michael Perthu, Copenhagen (DK)

(73) Assignee: UNION MEDICO APS, Copenhagen N (DK)

( * ) Notice: Subject to any disclaimer, the term of this patent is extended or adjusted under 35 U.S.C. 154(b) by 184 days.

(21) Appl. No.: 16/961,777

(22) PCT Filed: Feb. 7, 2019

(86) PCT No.: PCT/EP2019/052990
§ 371 (c)(1),
(2) Date: Jul. 13, 2020

(87) PCT Pub. No.: WO2019/158426
PCT Pub. Date: Aug. 22, 2019

(65) Prior Publication Data
US 2021/0060265 A1 Mar. 4, 2021

(30) Foreign Application Priority Data
Feb. 13, 2018 (EP) ..................... 18156569

(51) Int. Cl.
*A61M 5/32* (2006.01)
*A61M 5/46* (2006.01)
*A61M 5/24* (2006.01)

(52) U.S. Cl.
CPC ............ *A61M 5/3287* (2013.01); *A61M 5/24* (2013.01); *A61M 5/46* (2013.01); *A61M 2005/2488* (2013.01); *A61M 2005/2492* (2013.01)

(58) Field of Classification Search
CPC .................. A61M 5/3287; A61M 5/46; A61M 2005/2492; A61M 2005/2488
See application file for complete search history.

(56) References Cited

U.S. PATENT DOCUMENTS

| | | | | |
|---|---|---|---|---|
| 2,918,063 | A * | 12/1959 | Tucker | A61M 5/3287 604/157 |
| 2010/0185178 | A1 * | 7/2010 | Sharp | A61M 5/3129 604/110 |
| 2015/0080811 | A1 * | 3/2015 | Wieselblad | A61M 5/3155 604/207 |
| 2015/0088067 | A1 * | 3/2015 | Limaye | A61M 5/46 604/117 |

FOREIGN PATENT DOCUMENTS

| | | | |
|---|---|---|---|
| WO | 01/41837 | A1 | 6/2001 |
| WO | 2012/175082 | A1 | 12/2012 |
| WO | 2015/014363 | A2 | 2/2015 |
| WO | 2015/131903 | A1 | 9/2015 |
| WO | WO-2015131903 | A1 * | 9/2015 ............ A61M 5/002 |

OTHER PUBLICATIONS

International Search Report dated May 7, 2019 and Written Opinion in corresponding International application No. PCT/EP2019/052990; 11 pages.

* cited by examiner

*Primary Examiner* — Jenna Zhang
(74) *Attorney, Agent, or Firm* — Maier & Maier, PLLC

(57) ABSTRACT

An injection device adapted for injecting a durable or pre-filled pen device along an injection direction defining an injection axis. The injection device is provided with a certain holder and locking mechanism for fixing and holding a pen device in a correct position for injection into human skin.

7 Claims, 3 Drawing Sheets

INJECTION DEVICE AND ADAPTOR

FIELD

Figure 1:
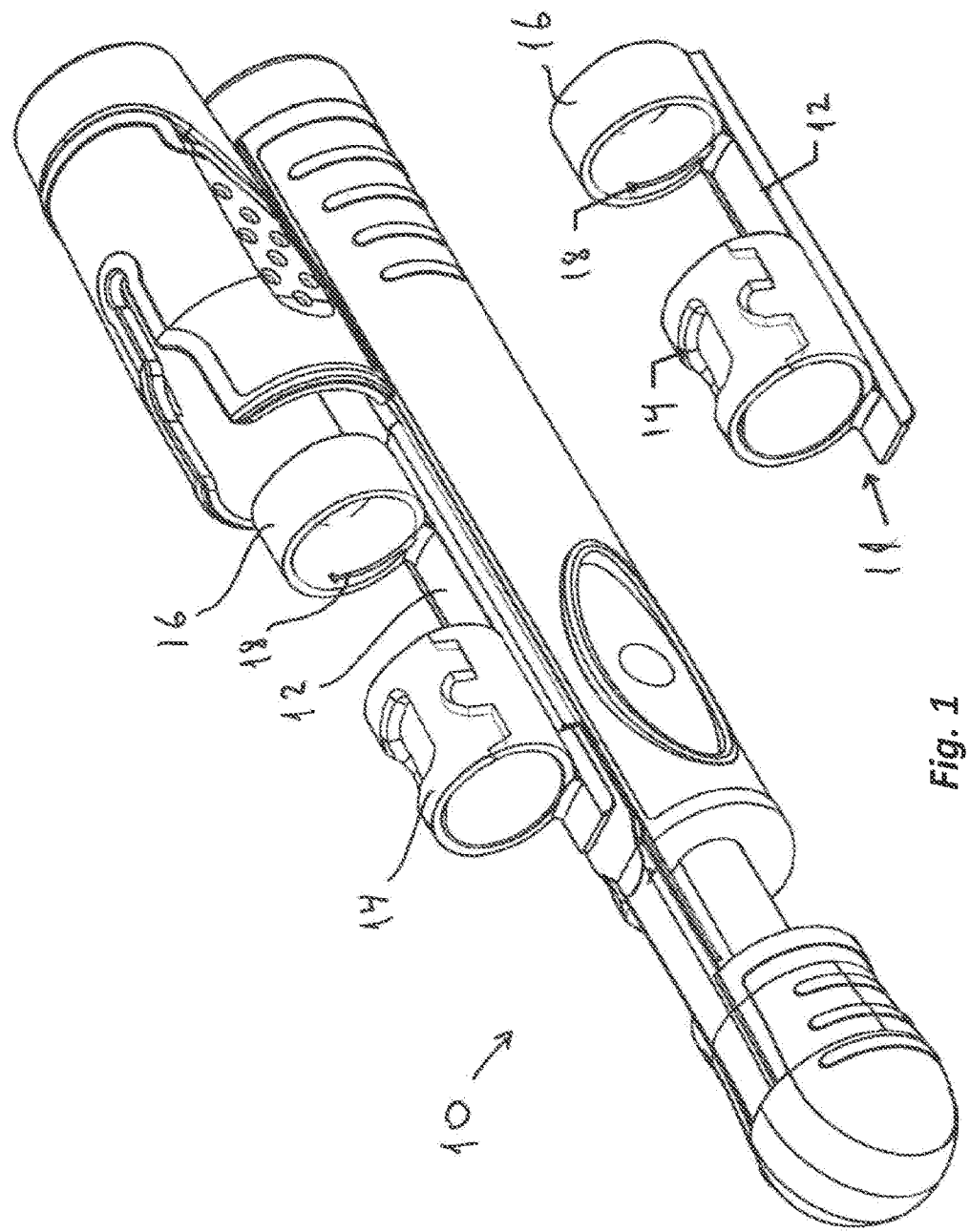

The present invention relates to an injection device adapted for injecting a durable or pre-filled pen device along an injection direction defining an injection axis, as well as a method of injection using this injection device together with the pen device. The present invention also concerns a holder adapted for holding a pen device for use in an injection device.

BACKGROUND

Many people are in their daily live faced with the task of injecting hypodermic syringes. The purpose of these injections may both be for therapeutic treatment, prophylactic treatment or cosmetic treatment. Examples of therapeutic treatment are subcutaneous delivery of insulin for diabetics, subcutaneous delivery of epinephrine for people suffering from Anaphylaxis, intramuscular and/or subcutaneous delivery of antibiotics for treating infections, and intramuscular delivery of drugs for treatment of Multiple Sclerosis. Examples of prophylactic treatment are intramuscular delivery of vitamins, subcutaneous delivery of vaccines, and intramuscular and/or subcutaneous delivery of medicaments.

The injections may be performed by the users themselves or by medical professionals. In both cases it is desirable to secure that the injections are performed in a safe and controlled manner This may be achieved by using an automatic injecting device configured to automatically inject a syringe.

WO2015/014363 discloses an injection device for a hypodermic syringe for injecting a hypodermic syringe along an injection direction defining an injection axis, wherein said injecting device comprises:
a housing for being positioned at the skin of a user, wherein said housing comprises a first tubular element having an upper opening; and
a movable element movably arranged relative to said housing between a retracted position and an injection position, wherein said movable element comprises a hypodermic syringe holder for holding a hypodermic syringe,
wherein said movable element comprises a first portion arranged to slide inside said first tubular element of said housing, a second portion arranged to slide at a first outer surface of said housing, and a connection portion connecting said first portion with said second portion, wherein said movable element extends out of said upper opening of said first tubular element.

WO2015/131903 discloses an injection device for a hypodermic syringe along an injection direction defining an injection axis, wherein said injecting device comprises:
a housing for being positioned at the skin; and
a movable element movably arranged relative to said housing between a retracted position and an injection position, said movable element comprising: a hypodermic syringe holder for holding a hypodermic syringe;
wherein said injection device further comprises an injection depth modifying element configured to modify the injection depth of the injection device.

Summary

The present invention concerns an injection device adapted for injecting a durable or pre-filled pen device along an injection direction defining an injection axis, wherein said injecting device comprises:
a) a housing adapted for being positioned on skin of a human subject, wherein said housing comprises a tubular element having a first end for being positioned on the skin and a second upper opening opposite the first end; and
b) a movable element movably arranged relative to the housing between a retracted position and an injection position, wherein the movable element comprises a holder adapted for holding the pen device, wherein the movable element comprises a first portion arranged to slide inside the first tubular element of the housing, a second portion arranged to slide at a first outer surface of the housing, and a connection portion connecting the first portion with the second portion, wherein the movable element extends out of the upper opening of the first tubular element,
wherein the holder comprises a first holding part closest to the first end of the housing and a second holding part, wherein the first holding part has a first means for engaging and fixing the pen device in a correct position for injection, and the second holding part is configured to lock the pen device and prevent the pen device from moving relative to the movable element of the injection device.

In an embodiment of the first aspect, the pen device has an outer circumference, wherein a second means for engaging with the first means of the first holding part and fixing the pen device in the correct position for injection is located at the outer circumference. Thus, for instance, the pen device may have a shoulder or other protrusion that may extent fully or partly in the circumference, and which protrusion can engage and snap-lock together with the first means of the first holding part, wherein the first means is for instance a cavity corresponding to the protrusion for snap-lock engagement.

The term "a durable or pre-filled pen device" as used herein means a pen device which contains a syringe and a chamber with the relevant medicine, such medicines may be insulin or a hormone, such as growth hormone, wherein the chamber may be pre-filled with the medicine or contains a cartridge with the medicine making it a durable pen device. Examples of pen devices are Novopen®, Novopen Echo®, NovoRapid®, FlexPro®, NordiFlex®, NordiPen®, NordiLet®, Xultophy®, FlexPen®, Flextouch®, Clickstar®, Toujeo Solostar®, Apidra®, Lantus Solostar®, and Humalog Kwikpen® and each of these pen devices are a suitable embodiment of the pen device to be used together with the injection device of the present invention, such as in the injection device system of the present invention. Examples of specific medicines are insulin, insulin analogs, Genotropin, Glotropin, Hygetropin, IGF1 Global, Norditropin, Protophin, Somatropin, and Unitropin.

The term "an injection device adapted for injecting a durable or pre-filled pen device along an injection direction defining an injection axis" as used herein means an injection device as described in WO2015/014363 as well as in WO2015/131903, except that the device is now adapted to hold and fix a durable or pre-filled pen device.

In an embodiment of the present invention, the second holding part (14) comprises a lower part and an upper part, wherein the upper part and lower part are configured to snap-lock and lock the pen device. Typically, such upper and lower parts are as described in WO2015/131903, see for instance FIGS. 4a, 7a-e and 8a-d and the description giving detailed explanation. Please also refer to present FIG. 1.

Figure 2:
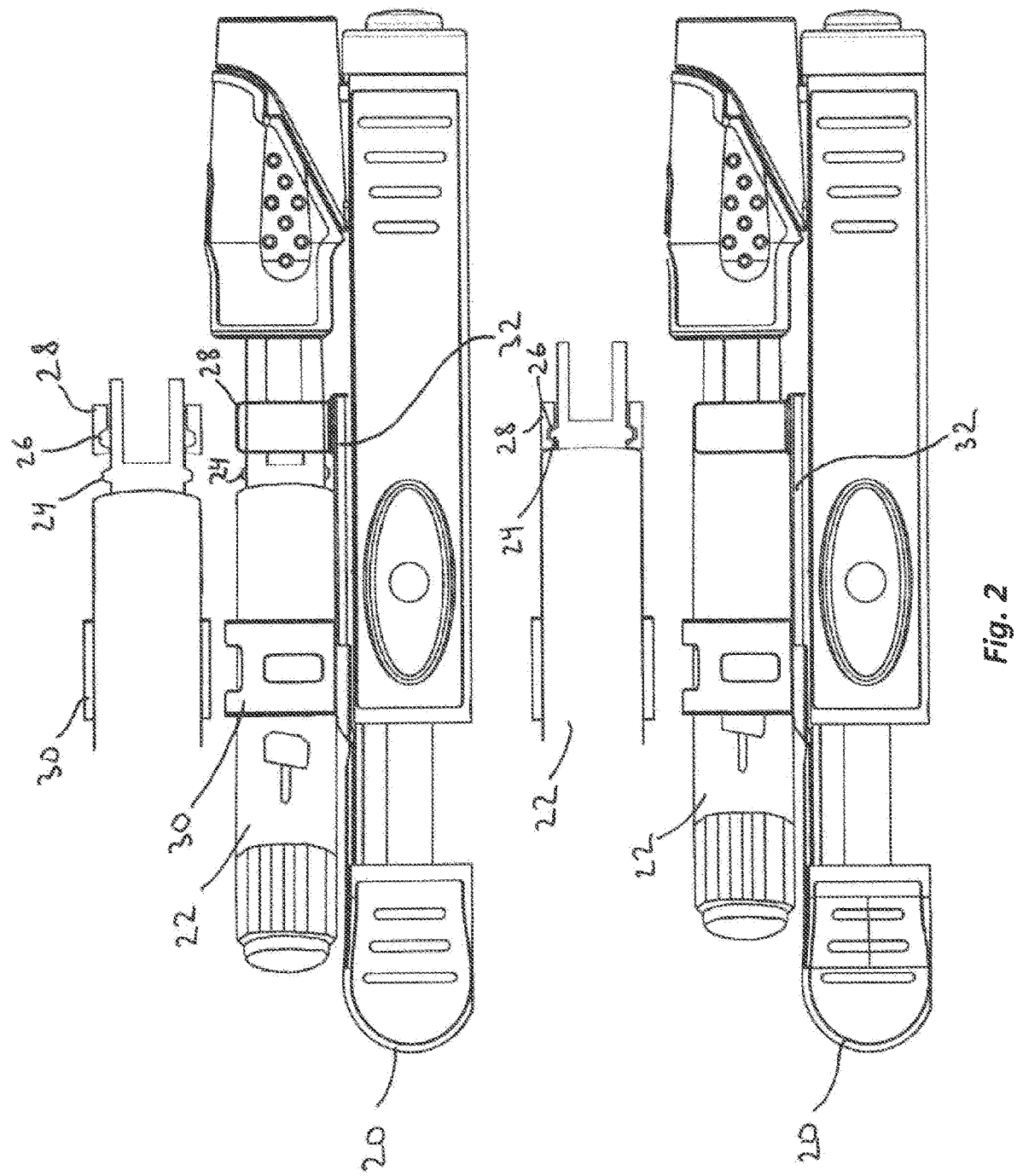

In another embodiment of the present invention the first means of the first holding part and the second means of the pen device are adapted to engage in a snap-lock. Typically, such first means is a threaded type lock (18) as shown in FIG. 1, or a cavity (26) as shown in FIG. 2. Further, the second means of the pen device are corresponding threaded type lock (not shown), or protrusion (24) as shown in FIG. 2. In a further embodiment of the present invention the first means of the first holding part and the second means of the pen device are adapted to engage in a conic lock.

In a further embodiment of the present invention, the first means of the first holding part and the second means of the pen device are adapted to engage in a threaded type lock. Such threaded type lock (18) is shown in FIG. 1.

In a still further embodiment of the present invention the first means of the first holding part comprises a cavity and the second means of the pen device comprises a protrusion, wherein the cavity and protrusion are adapted to engage in the snap-lock. Such cavity (26) and protrusion (24) and engagement is shown in FIG. 2. In another embodiment of the present invention the first means of the first holding part comprises a protrusion and the second means of the pen device comprises a cavity, wherein the cavity and protrusion are adapted to engage in the snap-lock. Other snap-lock systems are known to the skilled person in the art.

In a further embodiment of the present invention the durable or pre-filled pen device is a pre-filled pen.

In a still further embodiment of the present invention the durable or pre-filled pen device is a durable pen.

Figure 3:
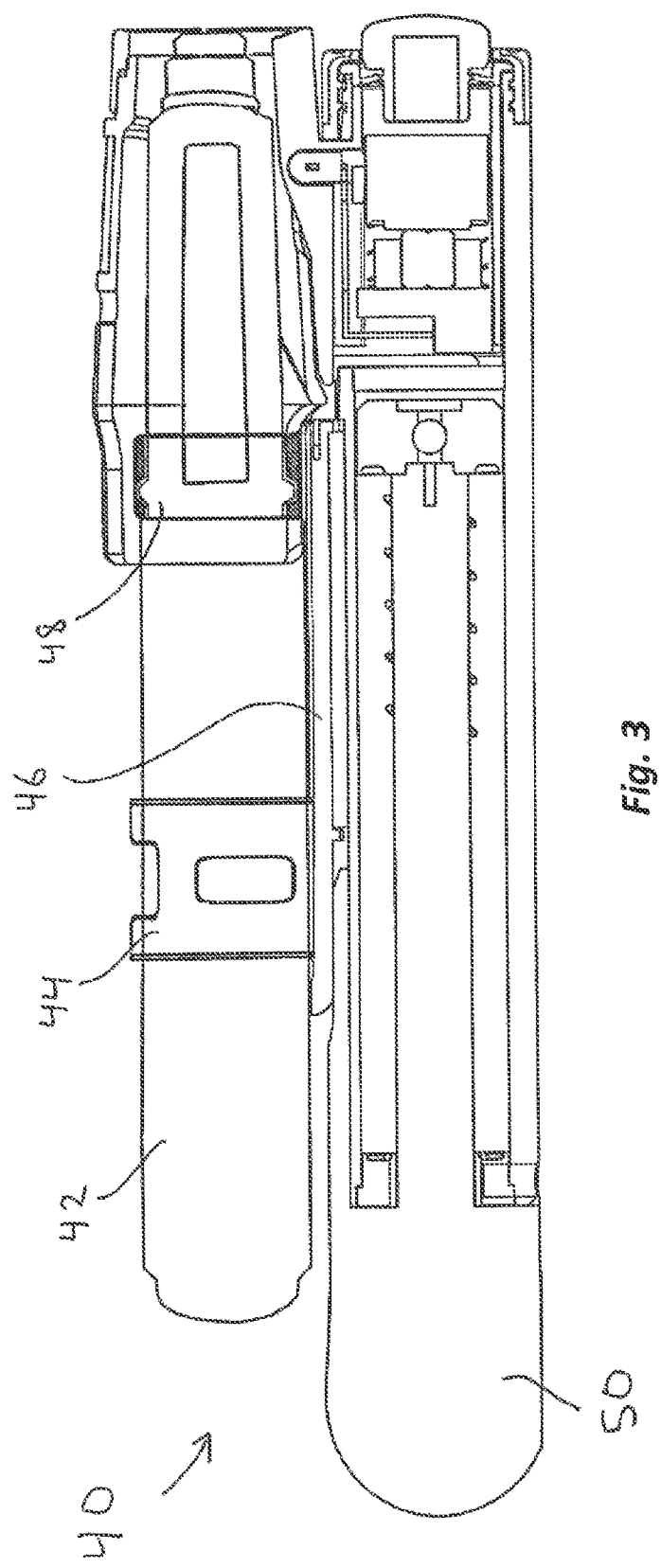

In a further aspect, the present invention concerns an injection device system adapted for injecting a pre-filled pen device along an injection direction defining an injection axis, wherein said injecting device system comprises:
a) a housing adapted for being positioned on skin of a human subject, wherein said housing comprises a tubular element having a first end for being positioned on the skin and a second upper opening opposite the first end; and
b) a movable element movably arranged relative to the housing between a retracted position and an injection position, wherein the movable element comprises a holder adapted for holding the pen device, wherein the movable element comprises a first portion arranged to slide inside the first tubular element of the housing, a second portion arranged to slide at a first outer surface of the housing, and a connection portion connecting the first portion with the second portion, wherein the movable element extends out of the upper opening of the first tubular element,
c) the pre-filled pen device containing a medicine,
wherein the holder comprises a first holding part closest to the first end of the housing and a second holding part, wherein the first holding part has a first means for engaging and fixing the pen device in a correct position for injection, and the second holding part is configured to lock the pen device and prevent the pen device from moving relative to the movable element of the injection device,
wherein the pen device has an outer circumference, wherein a second means for engaging with the first means of the first holding part and fixing the pen device in the correct position for injection is located at the outer circumference. It is to be understood that any one of the above embodiments in connection with the first aspect of the present invention also applies for the injection device of the system. An embodiment of this system is shown in FIG. 3.

In a still further aspect, the present invention relates to a holder adapted for holding a pen device for use in an injection device, comprising a first holding part and a second holding part, wherein the first holding part has a first means for engaging and fixing the pen device in a correct position for injection, and the second holding part is configured to lock the pen device and prevent the pen device from moving relative to the holder. This holder can be used with any injection device, such as autoinjection devices, and represents a break-through in injection device systems for using pre-filled pen devices. The adaptor (herein also claimed as a holder adapted for holding a pen device for use in an injection device) is to be used with i.a. disposable or reusable prefilled pen systems for e.g. insulin/hormone and other multidose therapies. The present adaptor when configured to be a part of an injection device, ensure a high level of patient comfort, maximum patient acceptance, it is a user-friendly-self-injection-systems, and easier to use with less injection pain.

In a further aspect, the present invention concerns a method of injecting a durable or pre-filled pen device, comprising:
i) providing an injection device according the above aspect as well as any one of the embodiments, wherein the movable element is in the retracted position;
ii) arranging the pen device containing a medicine in the first holding part and engaging the first and second means for fixing the pen device in the correct position for injection;
iii) arranging the pen device in the second holding part and locking the pen device to prevent the pen device from moving relative to the movable element of the injection device,
iv) positioning the injection device at the skin of a human subject;
pushing a release mechanism on the injection device, whereby the movable element moves to said injection position and the medicine of the pen device is injected.

The invention will now be described more fully with reference to the appended drawings illustrating typical embodiments of the injection device and the holder of the present invention.

BRIEF DESCRIPTION

FIG. 1 may show an embodiment of injection device;
FIG. 2 may show another embodiment of an injection device;
FIG. 3 may show an embodiment of an injection system.

These drawings are by no means limiting the scope of the present invention and are only intended to guide the skilled person for better understanding of the present invention.

DETAILED DESCRIPTION

FIG. 1 illustrates an injection device (10) as described in WO2015/014363, see in particular FIGS. 18-23 and corresponding text in the description. As shown the syringe holder (314) of FIGS. 18-23 of WO2015/014363 has been replaced by a holder (12) adapted for holding the pen device (not shown), wherein a first holding part (16) is shown with a threaded type lock (18) for engagement of a pen device (not shown). Further a second holding part (14) as part of the holder (12) is configured to lock the pen device and prevent the pen device from moving relative to the movable element of the injection device. Such second holding part (14) is also illustrated in WO2015/131903, see for instance FIGS. 4*a*, 7*a-e*, and 8*a-d* and corresponding text in the description. Further shown is the holder (11) adapted for holding the pen device, which holder (11) can be used in connection with any injector device, such as autoinjector devices, for securing best possible patient compliance.

FIG. 2 illustrates an injection device (20) as described in WO2015/014363, see in particular FIGS. 18-23 and corresponding text in the description. As shown the syringe holder (314) of FIGS. 18-23 of WO2015/014363 has been replaced by a holder (32) adapted for holding the pen device (22), wherein a first holding part (28) is shown with a cavity (24) for engagement of a protrusion (24) of the pen device (22). Further a second holding part (30) as part of the holder (32) is configured to lock the pen device and prevent the pen device from moving relative to the movable element of the injection device. The second holding part (30) is more detailed described in WO2015/131903, see for instance FIGS. 4a, 7a-e, and 8a-d and corresponding text in the description. The two identical injector devices are shown with the pen device inserted but not engaged on top and when the pen device is engaged so that protrusion (24) is engaged and fixed in cavity (26), and wherein the holder (30) has locked the pen device (22) at bottom.

FIG. 3 illustrates an injection device system (40) wherein a pre-filled pen device (42) is fixed by snap-lock in first holding part (48) and locked by second holding part (44), wherein the first (48) and second holding part (44) are part of the holder (46) adapted to hold and keep the pen device locked in the correct position as part of the injection device (50) for injection into human skin.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

Recitation of ranges of values herein are merely intended to serve as a short method of referring individually to each separate value falling within the range, unless other-wise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about", where appropriate).

All methods described herein can be performed in any suitable order unless otherwise indicated herein or otherwise clearly contradicted by context.

The terms "a" and "an" and "the" and similar referents as used in the context of de-describing the invention are to be construed to insert both the singular and the plural, unless otherwise indicated herein or clearly contradicted by context. Thus, "a" and "an" and "the" may mean at least one, or one or more.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

Throughout the description when "selected from" or "selected from the group consisting of" is used it also means all possible combinations of the stated terms, as well as each individual term.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter re-cited in the aspects or claims presented herein to the maximum extent permitted by applicable law.

The features disclosed in the foregoing description may, both separately and in any combination thereof, be material for realizing the invention in diverse forms thereof.

I claim:

1. An injection device adapted for injecting a pen injector device along an injection direction defining an injection axis, comprising:
   a housing adapted to be positioned on skin of a human subject, wherein said housing includes a tubular element having a first end positioned on the skin and a second upper opening opposite the first end; and
   a movable element movably arranged relative to the housing between a retracted position and an injection position, wherein the movable element includes a holder adapted for holding the pen injector device, wherein the movable element includes a first portion arranged to slide inside the tubular element of the housing, a second portion arranged to slide at a first outer surface of the housing, and a connection portion connecting the first portion with the second portion, wherein the movable element extends out of the second upper opening of the tubular element,
   wherein the holder includes a first holding part closest to the first end of the housing and a second holding part, wherein the first holding part has a first element for engaging and fixing the pen injector device in a correct position for injection, and the second holding part is configured to lock the pen injector device and prevent the pen injector device from moving relative to the movable element of the injection device, and
   wherein the first element of the first holding part is adapted to engage in a threaded-type lock with a second element of the pen injector device so that the pen injector device screws into the first element to engage with the first holding part.

2. The injection device of claim 1, wherein the second holding part includes a lower part and an upper part wherein the upper part and lower part are configured to snap-lock and lock the pen injector device.

3. The injection device of claim 1, wherein the first element of the first holding part includes an inner thread proceeding about an inner circumference of the first element, and the second element of the pen injector device comprises a corresponding thread engaging element which coincides with the inner thread, and wherein the inner thread and a corresponding thread engaging element are adapted to engage in the threaded-type lock.

4. The injection device of claim 1, wherein the pen injector device is a pre-filled pen injector.

5. The injection device of claim 1, wherein the pen injector device is a pen injector configured to accept replaceable cartridges.

6. An injection device system adapted for injecting pen injector device along an injection direction defining an injection axis, comprising:
- a housing adapted to be positioned on skin of a human subject, wherein said housing includes a tubular element having a first end for being positioned on the skin and a second upper opening opposite the first end; and
- a movable element movably arranged relative to the housing between a retracted position and an injection position, wherein the movable element includes a holder adapted for holding the pen injector device, wherein the movable element includes a first portion arranged to slide inside the tubular element of the housing, a second portion arranged to slide at a first outer surface of the housing, and a connection portion connecting the first portion with the second portion, wherein the movable element extends out of the second upper opening of the tubular element, wherein the pen injector device contains a medicine, wherein the holder includes a first holding part closest to the first end of the housing and a second holding part, wherein the first holding part has a first element for engaging and fixing the pen injector device in a correct position for injection, and the second holding part is configured to lock the pen injector device and prevent the pen injector device from moving relative to the movable element of the injection device, wherein the pen injector device has an outer circumference, wherein a second element of the pen injector device is adapted to engage with the first element of the first holding part to fix the pen injector device in the correct position for injecting and the second element of the pen injector device is located at the outer circumference, and wherein the first element of the first holding part is adapted to engage in a threaded-type lock with the second element of the pen injector device so that the pen injector device screws into the first element to threadedly engage with the first holding part.

7. A method of injecting a pen injector device, comprising:
- providing the injection device according to claim 1, wherein the movable element is in the retracted position;
- arranging the pen injector device containing a medicine in the first holding part and engaging the first and second elements for fixing the pen injector device in the correct position for injection;
- arranging the pen injector device in the second holding part and locking the pen injector device to prevent the pen injector device from moving relative to the movable element of the injection device,
- positioning the injection device at the skin of the human subject; and
- pushing a release mechanism on the injection device, whereby the movable element moves to said injection position and the medicine of the pen injector device is injected.

* * * * *